United States Patent
Rose et al.

(12)

(10) Patent No.: US 6,217,871 B1
(45) Date of Patent: Apr. 17, 2001

(54) ANTIGENIC EPITOPES WITH LYM-1 REACTIVITY AND USES THEREOF

(75) Inventors: Larry M. Rose, Carmichael; Claude F. Meares, Davis; Robert T. O'Donnell, Sacramento, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/181,896

(22) Filed: Oct. 28, 1998

(51) Int. Cl.⁷ ..................................................... A61K 39/00
(52) U.S. Cl. .................. 424/184.1; 530/326; 424/130.1; 424/133.1; 424/185.1
(58) Field of Search ..................................... 530/324–326; 424/130.1, 133.1, 184.1, 185.1

(56) References Cited

U.S. PATENT DOCUMENTS 5,976,551 * 11/1999 Mottez et al. .................. 424/195.11

FOREIGN PATENT DOCUMENTS

95/11702 * 5/1995 (WO) .

* cited by examiner

*Primary Examiner*—Sheela Huff
(74) *Attorney, Agent, or Firm*—Townsend & Townsend & Crew LLP (57) ABSTRACT

This invention provides novel peptide epitopes recognized by the non-Hodgkin's B cell lymphoma reactive Lym-1 antibody. These novel peptide epitopes are capable of generating antibodies directed against Lym-1 peptide epitope expressing B-NHL cells. This invention is also directed to the treatment of B-NHL.

13 Claims, 1 Drawing Sheet

ANTIGENIC EPITOPES WITH LYM-1 REACTIVITY AND USES THEREOF

FIELD OF THE INVENTION

This invention has identified novel peptide epitopes recognized by the B cell lymphoma-reactive Lym-1 antibody. Because Lym-1 specifically reacts with non-Hodgkin's B cell lymphoma cells, the invention provides an improved, accurate means to identify cancer patients potentially responsive to Lym-1 antibody used as a cytotoxic therapeutic reagent. The invention also provides methods of generating antibodies directed against non-Hodgkin's B cell lymphoma cells which can be used in the treatment of non-Hodgkin's B cell lymphoma.

INTRODUCTION

Low grade B-cell non-Hodgkin's lymphomas (B-NHL) represent a markedly heterogeneous group of lymphoproliferative disorders (Gaidano (1997) Leuk. Lymphoma 26 Suppl. 1:107–113; Gandini (1996) Cancer Genet Cytogenet. 86:120–123). A widely used treatment for these lymphomas involves administration of a B-NHL-specific antibody, called Lym-1. Lym-1 is a murine $IgG_{2a}$ monoclonal antibody. When conjugated to cytotoxic agents, Lym-1 targets and kills B-NHL lymphoma cells (see, e.g., Rose (1996) Cancer Immunol. Immunother. 43:26–30; Epstein (1987) Cancer Res. 47:830–840). Lym-1 has been radiolabeled with $^{131}I$ (see, e.g., DeNardo (1997) Cancer 80:2706–2711) and conjugated to the ribosome inactivating protein gelonin (see, e.g., O'Boyle (1995) J. Immunother. Emphasis Tumor Immunol. 18:221–230). However, these reagents are inherently toxic, and not all B-NHL patients have Lym-1 reactive cancer cells. Thus, there is a need for a means to identify which patients will be responsive to such immunotherapy. While Lym-1 binding is associated with the expression of HLA DR10 by a patient, unfortunately, the absence of DR10, does not consistently correlate with the presence or absence of the Lym-1 reactive epitope. In other words, Lym-1 can react with HLA DR molecules other than DR10. Thus, there is a great need for a means to quickly, efficiently, and accurately determine the presence of a Lym-1 reactive epitope in a B-NHL cancer patient. The present invention, which for the first time identifies Lym-1 reactive peptide epitopes, fulfills these and other needs.

Typically, no immune response is generated by the cancer patient against B-NHL cells. However, based on studies with other tumor specific antigens (e.g., PSA antigen in prostate cancer), identification of an immunogenic peptide, followed by its administration with adjuvant, can elicit a tumor-specific immune response (see, e.g., Correale (1998) J. Immunol. 161:3186–3194). See also, Gjertsen (1998) Vox Sang. 74 Suppl 2:489–495, who uses an immunogenic peptide from a carcinogenic, mutant ras polypeptide to generate an immune response to pancreatic- and colorectal adenocarcinomas. The present invention, by identifying Lym-1 reactive epitopes on B-NHL cells, provides such a therapeutic immunogenic peptide.

SUMMARY OF THE INVENTION

The invention for the first time provides a composition comprising an isolated or recombinant peptide comprising a subsequence of a Class II major histocompatibility molecule that generates an immune response to a non-Hodgkin's B cell lymphoma cell. The peptide of the invention has a structure comprising $R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$, wherein $R_1$ is Gln, Lys, or Arg; $R_2$ is Arg; $R_3$ and $R_4$ are members independently selected from the group consisting of all amino acids; $R_5$ is Ala, Glu, Asp, Val, Leu or Ile; $R_6$ and $R_7$ are members independently selected from the group consisting of all amino acids; $R_8$ is Thr; $R_9$, $R_{10}$, $R_{11}$, $R_{12}$, $R_{13}$, $R_{14}$, and $R_{15}$ are members independently selected from the group consisting of all amino acids; and, $R_{16}$ is Val.

In one embodiment, the peptide of the invention has a structure wherein $R_1$ is Gln, Lys, or Arg; $R_2$ is Arg; $R_3$ is Arg; $R_4$ is selected from the group consisting of all amino acids; $R_5$ is Ala; $R_6$ and $R_7$ are members independently selected from the group consisting of all amino acids; $R_8$ is Thr; $R_9$ is selected from the group consisting of all amino acids; $R_{10}$ is Cys; $R_{11}$, $R_{12}$, $R_{13}$, $R_{14}$, and $R_{15}$ are members independently selected from the group consisting of all amino acids; and, $R_{16}$ is Val (SEQ ID NO: 1). In a preferred embodiment, the immunogenic peptide comprises a structure wherein $R_1$ is Gln, Lys, or Arg; $R_2$ is Arg; $R_3$ is Arg; $R_4$ is Ala; $R_5$ is Ala; $R_6$ is Val; $R_7$ is Asp; $R_8$ is Thr; $R_{is\ Tyr;\ R10}$ is Cys; $R_{11}$ is Arg; $R_{12}$ is His; $R_{13}$ is Asn; $R_{14}$ is Tyr; $R_{15}$ is Gly, and $R_{16}$ is Val (SEQ ID NO: 2).

In alternative embodiments, the composition further comprises a pharmaceutically acceptable excipient and an adjuvant.

The composition of the invention can generate an immune response to a non-Hodgkin's lymphoma cell (B-NHL), including, e.g., a B-cell chronic lymphocytic leukemia/small lymphocytic lymphoma (B-CCL/SLL) cell, a lymphoplasmacytoid lymphoma (LPL) cell, a follicular lymphoma (FL) cell, a mucosa-associated lymphoid tissue lymphoma (MALTL) cell, a splenic lymphoma with villous lymphocytes (SLVL) cell and a mantle cell lymphoma cell.

The invention also provides a method for detecting a nucleic acid in a biological sample, wherein the nucleic acid encodes a peptide capable of specifically binding to a Lym-1 antibody. The method of the invention comprises contacting the sample with an oligonucleotide primer pair capable of amplifying a subsequence of an MHC nucleic acid, which subsequence encodes a polypeptide comprising a peptide of the invention, as described above; amplifying the nucleic acid; and, detecting the amplified nucleic acid. In alternative embodiments, the MHC gene is HLA-DR 10 and the subsequence encodes a peptide wherein $R_1$ is Gln, Lys, or Arg; $R_2$ is Arg; $R_3$ is Arg; $R_4$ is Ala; $R_5$ is Ala; $R_6$ is Val; $R_7$ is Asp; $R_8$ is Thr; $R_9$ is Tyr; $R_{10}$ is Cys; $R_{11}$ is Arg; $R_{12}$ is His; $R_{13}$ is Asn; $R_{14}$ is Tyr; $R_{15}$ is Gly, and $R_{16}$ is Val (SEQ ID NO: 2).

In the methods, the biological sample can comprise a B cell, or specifically, a B lymphocytic non-Hodgkin's lymphoma cell (B-NHL). The B-NHL cell can be a B-cell chronic lymphocytic leukemia/small lymphocytic lymphoma (B-CCL/SLL) cell, a lymphoplasmacytoid lymphoma (LPL) cell, a follicular lymphoma (FL) cell, a mucosa-associated lymphoid tissue lymphoma (MALTL) cell, a splenic lymphoma with villous lymphocytes (SLVL) cell and a mantle cell lymphoma cell. In alternative embodiments the biological sample can be a body fluid sample or a biopsy sample; and the body fluid sample can be a blood sample.

The invention further provides a kit for detecting a nucleic acid in a biological sample, wherein the nucleic acid encodes a peptide capable of specifically binding to a Lym-1 antibody. The kit comprises an oligonucleotide primer pair capable of amplifying a subsequence of an MHC gene or gene product, which subsequence encodes a polypeptide comprising a peptide of the invention. In alternative embodiments, the MHC gene can be HLA-DR 10; and, the peptide can comprise a structure wherein $R_1$ is Gln, Lys, or Arg; $R_2$ is Arg; $R_3$ is Arg; $R_4$ is Ala; $R_5$ is Ala; $R_6$ is Val; $R_7$ is Asp; $R_8$ is Thr; $R_9$ is Tyr; $R_{10}$ is Cys; $R_{11}$ is Arg; $R_{12}$ is His; $R_{13}$ is Asn; $R_{14}$ is Tyr; $R_{15}$ is Gly, and $R_{16}$ is Val (SEQ ID NO: 2).

In another embodiment, the kit of the invention can further comprise an instructional material teaching a use of the kit, wherein the instructional material indicates that the kit is used for the detection of nucleic acid encoding a peptide reactive with a Lym-1 antibody and that the polypeptide is associated with non-Hodgkin's B cell lymphomas.

The invention also provides a method for detecting an antibody reactive with a non-Hodgkin's B cell lymphoma (B-NHL) cell. The method comprises contacting a sample, which can be a biological sample, with a composition of the invention under immunologically reactive conditions, and then detecting whether an antibody has specifically bound to the composition. In one embodiment, the composition comprises a peptide having a structure wherein $R_1$ is Gln, Lys, or Arg; $R_2$ is Arg; $R_3$ is Arg; $R_4$ is Ala; $R_5$ is Ala; $R_6$ is Val; $R_7$ is Asp; $R_8$ is Thr; $R_9$ is Tyr; $R_{10}$ is Cys; $R_{11}$ is Arg; $R_{12}$ is His; $R_{13}$ is Asn; $R_{14}$ is Tyr; $R_{15}$ is Gly, and $R_{16}$ is Val (SEQ ID NO: 2). In various embodiments of this method, the antibody is generated by a recombinant nucleic acid library, the recombinant nucleic acid is a phage display library, and the composition is fixed to a solid surface.

The invention further provides a method for generating an antibody reactive with a non-Hodgkin's B cell lymphoma (B-NHL) cell. The method comprises administering an immunogenically effective amount of a composition of the invention to a mammal. The composition can comprise a peptide having a structure wherein $R_1$ is Gln, Lys, or Arg; $R_2$ is Arg; $R_3$ is Arg; $R_4$ is Ala; $R_5$ is Ala; $R_6$ is Val; $R_7$ is Asp; $R_8$ is Thr; $R_9$ is Tyr; $R_{10}$ is Cys; $R_{11}$ is Arg; $R_{12}$ is His; $R_{13}$ is Asn; $R_{14}$ is Tyr; $R_{15}$ is Gly, and $R_{16}$ is Val (SEQ ID NO: 2). The B-NHL cell can be a B-cell chronic lymphocytic leukemia/small lymphocytic lymphoma (B-CCL/SLL) cell, a lymphoplasmacytoid lymphoma (LPL) cell, a follicular lymphoma (FL) cell, a mucosa-associated lymphoid tissue lymphoma (MALTL) cell, a splenic lymphoma with villous lymphocytes (SLVL) cell and a mantle cell lymphoma cell.

The invention provides an immunogenic composition capable of eliciting an immunogenic response directed to a polypeptide epitope, wherein the epitope comprises an amino acid sequence having a structure comprising $R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$, wherein $R_1$ is Gln, Lys, or Arg; $R_2$ is Arg; $R_3$ and $R_4$ are members independently selected from the group consisting of all amino acids; $R_5$ is Ala, Glu, Asp, Val, Leu or Ile; $R_6$ and $R_7$ are members independently selected from the group consisting of all amino acids; $R_8$ is Thr; $R_9$, $R_{10}$, $R_{11}$, $R_{12}$, $R_{13}$, $R_{14}$, and $R_{15}$ are members independently selected from the group consisting of all amino acids; and, $R_{16}$ is Val. In one embodiment, the epitope comprises a sequence wherein $R_1$ is Gln, Lys, or Arg; $R_2$ is Arg; $R_3$ is Arg; $R_4$ is Ala; $R_5$ is Ala; $R_6$ is Val; $R_7$ is Asp; $R_8$ is Thr; $R_9$ is Tyr; $R_{10}$ is Cys; $R_{11}$ is Arg; $R_{12}$ is His; $R_{13}$ is Asn; $R_{14}$ is Tyr; $R_{15}$ is Gly, and $R_{16}$ is Val (SEQ ID NO: 2). The immunogenic response can generate antibodies (i.e., a humoral response) specific for the polypeptide epitope. Alternatively, the immunogenic response can generate an epitope specific cellular response.

The invention further provides a method of inducing an immunogenic response directed to a polypeptide epitope, comprising administering an immunogenically effective amount of a composition comprising a polypeptide epitope to a mammal, wherein the epitope comprises an amino acid sequence having a structure comprising $R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$, wherein $R_1$ is Gln, Lys Arg; $R_2$ is Arg; $R_3$ and $R_4$ are members independently selected from the group consisting of all amino acids; $R_5$ is Ala, Glu, Asp, Val, Leu or Ile; $R_6$ and $R_7$ are members independently selected from the group consisting of all amino acids; $R_8$ is Thr; $R_9$, $R_{10}$, $R_{11}$, $R_{12}$, $R_{13}$, $R_{14}$, and $R_{15}$ are members independently selected from the group consisting of all amino acids; and, $R_{16}$ is Val. In one embodiment, the epitope comprises an amino acid sequence having a structure wherein $R_1$ is Gln, Lys, or Arg; $R_2$ is Arg; $R_3$ is Arg; $R_4$ is Ala; $R_5$ is Ala; $R_6$ is Val; $R_7$ is Asp; $R_8$ is Thr; $R_9$ is Tyr; $R_{10}$ is Cys; $R_{11}$ is Arg; $R_{12}$ is His; $R_{13}$ is Asn; $R_{14}$ is Tyr; $R_{15}$ is Gly, and $R_{16}$ is Val (SEQ ID NO: 2). The immunogenic response can generate antibodies (i.e., a humoral response) specific for the polypeptide epitope. Alternatively, the immunogenic response can generate an epitope specific cellular response. In various embodiments, the method involves administering the immunogenic composition to a human, a mouse or a rabbit.

A further understanding of the nature and advantages of the present invention may be realized by reference to the remaining portions of the specification, the figures and claims.

All publications, patents and patent applications cited herein are hereby expressly incorporated by reference for all purposes.

DETAILED DESCRIPTION OF THE INVENTION

The invention is based at least in part on the discovery of peptide epitopes recognized by the non-Hodgkin's B cell lymphoma (B-NHL)-reactive Lym-1 antibody. Because Lym-1 specifically reacts with B-NHL cells, the invention provides an improved, accurate means to identify which B-NHL patients will be responsive to a therapeutic Lym-1 antibody. The invention, by identifying these novel Lym-1 epitopes, also provides methods of generating an immune response, particularly antibodies, directed against B-NHL cells bearing the Lym-1 epitope.

In one embodiment, these peptides are incorporated into immunogenic compositions and administered to mammals, e.g., non-human animals, to generate antibodies with high affinity for B-NHL cells expressing Lym-1 epitopes. These antibodies are reactive with all Lym-1 epitope expressing cancer cells, including B-cell chronic lymphocytic leukemia/small lymphocytic lymphoma (B-CCL/SLL), lymphoplasmacytoid lymphomas (LPL), follicular lymphomas (FL), mucosa-associated lymphoid tissue lymphomas (MALTL), splenic lymphoma with villous lymphocytes (SLVL), and mantle cell lymphomas. In another embodiment, the immunogenic compositions of the invention are administered therapeutically to cancer patients with a B cell lymphoma expressing a Lym-1 epitope.

The invention further provides means to identify patients who will be responsive to Lym-1 antibody therapy. Because the novel peptides of the invention comprise the peptide epitope recognized by Lym-1, the invention provides an improved, accurate means to identify cancer patients potentially responsive to Lym-1 antibody used as a cytotoxic therapeutic reagent. The polymerase reverse transcriptase (PCR)-based methods and kits are especially needed for pre-screening B-NHL patients before such Lym-1 therapy.

Definitions

To facilitate understanding the invention, and to provide additional guidance to one of skill in the practice of the invention, a number of terms are defined below. Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2d ed. 1994); The Cambridge Dictionary of Science and Technology (Walker ed., 1988); and Hale & Marham, The Harper Collins Dictionary of Biology (1991). Although any methods and materials similar or equivalent to those described herein can be used in the practice or testing of the present invention, preferred methods and materials are described. As used herein, the following terms have the meanings ascribed to them unless specified otherwise.

The term "amino acid" as used herein refers to all naturally occurring amino acids and altered (i.e., a chemically modified naturally occurring amino acid) and synthetic, i.e., "mimetic" (defined below) amino acid residues which have substantially the same structure and function.

The term "amplifying" as used herein incorporates its common usage and refers to the use of any suitable amplification methodology for generating recombinant nucleic acid, as described in detail, below. For example, the invention provides methods and reagents (e.g., oligonucleotide PCR primer pairs) for amplifying nucleic acid encoding the novel Lym-1 epitope of the invention.

The term "antibody" refers to a peptide or polypeptide substantially encoded by an immunoglobulin gene or immunoglobulin genes, or fragments thereof, capable of specifically binding an epitope, see, e.g. Fundamental Immunology, Third Edition, W. E. Paul, ed., Raven Press, N.Y. (1993); Wilson (1994) J. Immunol. Methods 175:267–73; Yarmush (1992) J. Biochem. Biophys. Methods 25:85–97. One of skill will appreciate that antibody fragments may be isolated or synthesized de novo either chemically or by utilizing recombinant DNA methodology. The term antibody also includes "chimeric" antibodies either produced by the modification of whole antibodies or those synthesized de novo using recombinant DNA methodologies. Typically, such chimeric antibodies are "humanized antibodies," i.e., where the epitope binding site is generated from an immunized mammal, such as a mouse, and the structural framework is human. Immunoglobulins can also be generated using phage display libraries, and variations thereof, as described below.

The term "capable of generating an immune response to a non-Hodgkin's B cell lymphoma cell" means that the composition of the invention, when administered in an appropriate amount (the "immunogenically effective amount," defined and discussed, infra), either alone or in combination with another substance (such as, e.g., an adjuvant) or an immunologic carrier (defined infra), can elicit a humoral or cellular antigen-specific immune response.

The term "Lym-1 antibody" refers to a murine IgG$_{2a}$ monoclonal antibody that selectively binds an antigen, typically an HLA DR molecule (defined below), which is highly expressed on the surface of most B-NHL lymphomas (see, e.g., Rose (1996) Cancer Immunol. Immunother. 43:26–30; Epstein (1987) Cancer Res. 47:830–840). Lym-1 is used as an anti-cancer pharmaceutical after radiolabeling with a cytotoxic agent, such as, e.g., $^{131}$I (DeNardo (1997) supra), copper-67 (Denardo (1998) Anticancer Res. 18(4B):2779–88; Deshpande (1988) J. Nucl. Med. 29:217–225) or conjugation to the ribosome inactivating protein gelonin (O'Boyle (1995) supra; Boyle (1996) J. of Immunol. 18:221–230). The Lym-1 antigen is believed to be a variant form of HLA class II DR which is highly expressed on the surface of malignant B cells, but is found only at low levels in normal cells (see, e.g., Wurflein (1998) Cancer Res. 58:3051–8). That portion of the antigen that contacts the antibody is referred to as the "epitope." The present invention has, for the first time, defined the peptide which is the Lym-1 antibody reactive epitope.

The terms peptide and polypeptide include naturally occurring amino acids linked by peptide bonds and all "conservative variants," "analogs" and "mimetics" (defined below) which have substantially the same structure and function. Thus, the peptide and polypeptides of the invention comprising the Lym-1-reactive epitope include all conservative variants and mimetics that retain the ability to specifically bind to the Lym-1 antibody. A peptide or polypeptide with one or more of such "conservative substitutions" is also within the scope of the invention if it, as part of a composition, when administered in an immunogenically effective amount to a mammal, is capable of generating an antibody reactive with a B-NHL cell expressing the Lym-1 epitope. These include conservatively modified variations of the epitope's amino acid sequence, i.e., amino acid substitutions, additions or deletions of residues in the sequences provided herein, or substitution of amino acids with other amino acid residues or mimetics having similar properties (e.g., acidic, basic, positively or negatively charged, polar or non-polar, etc.) such that the substitutions of even critical amino acids does not substantially alter structure and activity. Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W); (see also, e.g., Creighton (1984) Proteins, W. H. Freeman and Company; Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions which alter, add or delete a single amino acid or a small percentage of amino acids in an encoded sequence can also be considered "conservatively modified variations." Routine experimentation will determine whether a conservative variant is within the scope of the invention, i.e., that its structure and/or function (i.e., its ability to generate an antibody reactive with a Lym-1 epitope-expressing B-NHL cell) is not substantially altered. An exemplary means to test for such reactivity is described herein.

The terms amino acid "mimetic" and "peptidomimetic" refer to a synthetic chemical compound which has substantially the same structural and functional characteristics of the Lym-1 reactive epitope of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity (i.e., capability of generating an antibody reactive with a Lym-1 epitope-expressing B-NHL cell). As with peptides and polypeptides of the invention which are conservative variants, routine experimentation will determine whether a mimetic is within the scope of the invention, and exemplary means to screen for such binding is described herein. Amino acid mimetic containing compositions can have any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, ie., to induce or stabilize a secondary structure, e.g., a beta turn, gamma turn, beta sheet, alpha helix conformation, and the like (see discussion, below, on Lym-1 reactive epitope secondary structure). A peptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267–357, "Peptide Backbone Modifications," Marcell Dekker, NY). A polypeptide can also be characterized as a mimetic by containing all or some non-natural residues in place of naturally occurring amino acid residues. Nonnatural residues are well described in the scientific and patent literature; a few exemplary nonnatural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2, 3-, or 4-pyreneylalanine; D- or L-3 thienelalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenyl-alanine; D- or L-p-biphenylphenylalanine; K- or L-p-methoxy-biphenyl-phenylalanine; D- or L-2-indole (alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a nonnatural amino acid include, e.g., thiazolyl, thiophenyl, pyrazolyl, benzimidazolyl, naphthyl, furanyl, pyrrolyl, and pyridyl aromatic rings. Mimetics of acidic amino acids can be generated by substitution by, e.g., non-carboxylate amino acids while maintaining a negative charge; (phosphono) alanine; sulfated threonine. Carboxyl side groups (e.g., aspartyl or glutamyl) can also be selectively modified by reaction with carbodiimides (R'—N—C—N—R') such as, e.g., 1-cyclohexyl-3(2-morpholinyl-(4-ethyl)carbodiimide or 1-ethyl-3(4-azonia-4,4-dimetholpentyl)carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids omithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclohexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl)propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups. A component of a natural polypeptide (e.g., the peptide of the invention) can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, generally referred to as the D-amino acid, or, the R- or S-form.

The term "Major Histocompatibility Complex gene" or "MHC gene" is used in its common usage and refers to genes and gene products encoding Major Histocompatibility Complex (MHC) molecules. Human MHC molecules can also be referred to as "Human Leukocyte Antigens" or HLA. Class II DR MHC molecules are heterodimers displayed on the cell surface of antigen processing/presenting cells (APCs), which include, e.g., human B cells. Cancer cells, e.g., B cell lymphomas, can also express DR molecules (see, e.g., Guy (1986) Br. J. Cancer 53:161–73; Rask (1991) Autoimmunity 8:237–44; Jones (1997) Curr. Opin. Immunol. 9:75–9).

The term "subsequence of a Class II major histocompatibility molecule" refers to a polypeptide or peptide that has a sequence that is less than a naturally occurring full length sequence of a Class II MHC polypeptide. For example, in alternative embodiments, the peptide of the invention is at least about 16 residues in length, at least about 25 residues in length, at least about 35 residues in length, at least about 45 residues in length, at least about 55 residues in length, at least about 65 residues in length, at least about 75 residues in length, and at least about 85 residues in length.

An "immunogen" refers to a compound or composition comprising a peptide, polypeptide or protein which is "immunogenic" when administered in an appropriate amount (the "immunogenically effective amount"), i.e., capable of eliciting, augmenting or boosting a cellular and/or humoral immune response, either alone or in combination or linked or fused to another substance (which can be administered at once or over several intervals). An immunogenically effective amount can vary depending on whether it is to be administered in intervals, versus a single dose. An immunogenic composition can be, e.g., a peptide of at least about 5 amino acids, a peptide of 10 amino acids in length, or a peptide of 16 amino acids in length. For example, the peptide of the invention if at least about 16 residues in length and is capable of generating an antibody specifically reactive with a Lym-1 epitope expressing B-NHL cell.

The immunogen can comprise a "carrier" polypeptide and a hapten, e.g., a fusion protein or a carrier polypeptide fused or linked (chemically or otherwise) to a peptide epitope (discussed below). The immunogen can be recombinantly expressed in an immunization vector, which can be simply naked DNA comprising the immunogen's coding sequence operably linked to a promoter. For example, the invention provides an immunogen capable of generating an antibody specifically reactive with a Lym-1 epitope expressing B-NHL cell.

An "immunological carrier" or "carrier" in the immunological context (as opposed to a carrier which is a nonactive composition for the purpose of formulating, storing or carrying a pharmaceutical) is an composition which, when linked, joined, chemically coupled or fused to a second composition (e.g., protein, peptide, polysaccharide or the like) boosts or augments the cellular or humoral response to the composition. Any physiologic mechanism can be involved in this augmentation or boosting of the immune response. An immunogenic carrier is typically a polypeptide linked or fused to a second composition (the second composition comprises the epitope/antigen intended to generate the immune response, e.g., the Lym-1 reactive peptide epitope of the invention). The carrier stimulates a cellular (T cell mediated) immune response that boosts or augments the humoral (B cell mediated, antibody-generating) immune response to the epitope-containing composition of interest (e.g., a peptide of the invention). These second compositions can be "haptens," which are typically defined as compounds of low molecular weight that are not immunogenic by themselves, but that, when coupled to carrier molecules, can elicit antibodies directed to epitopes on the hapten. For example, a peptide of the invention may be a hapten which, when conjugated to a carrier, becomes sufficiently immunogenic to generate an immune response. Alternatively, a peptide of the invention can be linked to a carrier simply to facilitate manipulation of the peptide in the generation of an immune response (see, e.g., Rondard (1997) Biochemistry 36:8962–8968).

The term "immunogenic response" refers to the generation of antibodies and/or a cell-mediated immune response elicited by the introduction of an immunogenic composition to a mammal.

As used herein, "isolated," when referring to a molecule or composition, such as, for example, a peptide or nucleic acid, means that the molecule or composition is separated from at least one other compound, such as a protein, other nucleic acids (e.g., RNAs), or other contaminants with which it is associated in vivo or in its naturally occurring state. Thus, a polypeptide or nucleic acid is considered isolated when it has been isolated from any other component with which it is naturally associated, e.g., cell membrane, as in a cell extract. An isolated composition can, however, also be substantially pure. An isolated composition can be in a homogeneous state and can be in a dry or an aqueous solution. Purity and homogeneity can be determined using a variety of analytical chemistry techniques such as, e.g., polyacrylamide gel electrophoresis (PAGE), high performance liquid chromatography (HPLC), and NMR spectroscopy.

The term "nucleic acid" or "nucleic acid sequence" refers to a deoxy-ribonucleotide or ribonucleotide oligonucleotide in either single- or double-stranded form. The term encompasses nucleic acids, i.e., oligonucleotides, containing known analogues of natural nucleotides which have similar or improved binding (hybridization) properties, for the purposes desired, e.g., amplification of nucleic acid encoding the Lym-1 reactive peptide of the invention, as the reference nucleic acid. The term also encompasses nucleic-acid-like structures with synthetic backbones, see e.g., Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923–1937; Antisense Research and Applications (1993, CRC Press), WO 97/03211; WO 96/39154; Mata (1997) Toxicol. Appl. Pharmacol. 144:189–197; Strauss-Soukup (1997) Biochemistry 36:8692–8698; Samstag (1996) Antisense Nucleic Acid Drug Dev 6:153–156).

The term "pharmaceutical composition" refers to a composition suitable for pharmaceutical use in a subject. The pharmaceutical compositions of this invention are formulations that comprise a pharmacologically effective amount of a composition comprising a peptide capable of generating an antibody specifically reactive to a Lym-1 epitope-expressing B-NHL cell, and a pharmaceutically acceptable carrier.

Nucleic Acids Encoding Lym-1 Reactive Peptides

This invention provides novel, immunogenic Lym-1-reactive peptides and nucleic acids encoding these peptides, including oligonucleotides capable of amplifying this newly identified Lym-1 epitope. Synthetic and recombinant forms of epitope-encoding nucleic acids are provided. The invention also provide means to express the epitope encoding nucleic acids of the invention to generate recombinant peptides and polypeptides; which can be expressed in vitro or in vivo. The invention provides for a variety of means of expressing the nucleic acids and proteins of the invention, including expression cassettes, vectors, cell lines, transgenic plants and animals, and the like.

The invention can be practiced in conjunction with any method or protocol known in the art, which are well described in the scientific and patent literature, see e.g., Sambrook, ed., Molecular Cloning: A Laboratory Manual (2nd ed.), Vols. 1–3, Cold Spring Harbor Laboratory, (1989) ("Sambrook"); Current Protocols in Molecular Biology, Ausubel, ed. John Wiley & Sons, Inc., New York (1997) ("Ausubel"); and, Laboratory Techniques in Biochemistry and Molecular Biology: Hybridization With Nucleic Acid Probes, Part I. Theory and Nucleic Acid Preparation, Tijssen, ed. Elsevier, N.Y. (1993) ("Tijssen").

Expression of Recombinant Lym-1 Reactive Peptides

The invention provides methods and reagents for recombinant expression of the novel Lym-1 reactive epitopes of the invention. The nucleic acids of the invention may be introduced into a genome or into the cytoplasm or a nucleus of a cell and expressed by a variety of conventional techniques, well described in the scientific and patent literature. For example, for expression of these nucleic acids, the invention incorporates expression cassettes, vectors, transgenic plants and animals, using constitutive and inducible transcriptional and translational cis-(e.g., promoters and enhancers) and trans-acting control elements. The expression of nucleic acid coding for Lym-1 reactive epitope can be achieved by operably linking the coding region to a promoter incorporating the construct into an expression cassette (such as an expression vector), and introducing the resultant construct into an in vitro reaction system or a suitable host cell or organism. See, e.g., Roberts (1987) Nature 328:731; Berger (1987) supra; Schneider (1995) Protein Expr. Purif. 6435:10; Sambrook, Tijssen or Ausubel. Product information from manufacturers of biological reagents and experimental equipment also provide information regarding known biological methods. The promoters and vectors used in this invention can be isolated from natural sources, obtained from such sources as ATCC or GenBank libraries, or prepared by synthetic or recombinant methods.

Amplification of Nucleic Acids Encoding Lym-1 Reactive Epitopes

The present invention provides oligonucleotide primers and probes that can hybridize specifically to nucleic acids to amplify sequences encoding the Lym-1 reactive epitopes of the invention. These oligonucleotide primer reagents can be used to identify and quantify such sequences. Utilizing these reagents, the invention provides a kit and a method for detecting in a biological sample a nucleic acid that encodes a peptide capable of specifically binding to a Lym-1 antibody. Illustrative PCR amplification methods for use in the kits and methods of the invention are described below.

Oligonucleotides can be used to amplify the epitope-encoding nucleic acid of the invention using a variety of hybridization techniques and conditions. One of skill in the art will appreciate that, whatever amplification method is used, if a quantitative result is desired, care must be taken to use a method that maintains or controls for the relative frequencies of the amplified nucleic acids. Suitable amplification methods include, but are not limited to: polymerase chain reaction, PCR (PCR Protocols, a Guide to Methods and Applications, ed. Innis, Academic Press, N.Y. (1990) and PCR STRATEGIES (1995), ed. Innis, Academic Press, Inc., N.Y. ("Innis")), ligase chain reaction (LCR) (Wu (1989) Genomics 4:560; Landegren (1988) Science 241:1077; Barringer (1990) Gene 89:117); transcription amplification (Kwoh (1989) Proc. Natl. Acad. Sci. U.S.A. 86:1173); self-sustained sequence replication (Guatelli (1990) Proc. Natl. Acad. Sci. U.S.A., 87:1874); Q Beta replicase amplification (Smith (1997) J. Clin. Microbiol. 35:1477–1491, automated Q-beta replicase amplification (Burg (1996) Mol. Cell. Probes 10:257–271); and other RNA polymerase mediated techniques (e.g., NASBA, Cangene, Mississauga, Ontario); see also Berger (1987) Methods Enzymol. 152:307–316, Sambrook, and Ausubel, as well as Mullis (1987) U.S. Pat. Nos. 4,683,195 and 4,683,202; Arnheim (1990) C&EN 36–47; Lomell (1989) J. Clin. Chem. 35:1826; Van Brunt (1990) Biotechnology 8:291–294; Wu (1989) Gene 4:560; and Sooknanan (1995) Biotechnology 13:563–564.

In these amplification techniques, oligonucleotide primers are designed to be complementary to the two borders of the DNA region to be amplified (see, e.g., Innis). Thus, the invention provides oligonucleotide primer pairs with sequences comprising the Lym-1-reactive peptide epitope sequences of the invention. The invention also provides oligonucleotide primer pairs capable of amplifying a subsequence of an MHC gene or gene product which contains the Lym-1-reactive peptide epitope sequences of the invention. Because the Lym-1 epitope is most commonly associated with the beta chain of the HLA DR10 allele, oligonucleotide primer pairs can include and can amplify subsequences of HLA DR10. Because the sequence of HLA DR10 is well known in the art, the skilled artisan can readily design oligonucleotide (PCR) primer pairs capable of amplifying subsequences of MHC genes, e.g., DR10, comprising sequences coding for the Lym-1 reactive epitopes of the invention. Furthermore, using public databases, the skilled artisan can readily search for additional HLA alleles containing Lym-1-reactive peptide epitope sequences of the invention and design appropriate oligonucleotide primer pairs capable of amplifying these MHC gene subsequences. See, e.g., Gongora (1996) Hum. Immunol. 51:23–31; Gongora (1997) J. Immunol. 159:6044–51; Rose (1996) supra.

In one embodiment, the invention provides a method for detecting a nucleic acid in a biological sample where the nucleic acid encodes a peptide capable of specifically binding to a Lym-1 antibody. In the sample, typically a cell (e.g. a B-NHL cell), is contacted with an oligonucleotide primer pair capable of amplifying the peptide-encoding nucleic acid (see, e.g., Bunce (1993) Hum. Immunol. 37:201–206). In a preferred embodiment, the PCR based methods and the kits of the invention are used to identify B-NHL patients who will be response to Lym-1 radiotherapy programs. This PCR based assay can be accomplished with a simple biological sample, i.e., from blood or saliva, that could be tested in parallel with, and eventually replace, the current need for a biopsy.

The invention's means to assess for Lym-1 reactivity provides a great improvement over the current criteria, which requires invasive biopsy or radioimaging with radioactive reagents. The present invention can be practiced with only a simple blood test. The results presented herein (see Example 1, below) confirm that Lym-1 binds preferentially to lymphoblastoid B-NHL cells over normal PBLs, which may help explain the impressive radio-immunodiagnostic and radio-immunotherapeutic results obtained so far in clinical trials of radiolabeled Lym-1.

Immunogenic Peptides and Polypeptides

This invention provides immunogenic peptides capable of generating an immune response, particularly antibodies, specifically directed to a Lym-1 epitope expressing B-NHL cell. These peptides can be isolated from natural sources (e.g., as fragments of MHC Class II DR polypeptides), synthetic, or recombinantly generated polypeptides. Lym-1 epitope expressing peptides and proteins can be recombinantly expressed in vitro or in vivo. The peptides, polypeptides and complexes of the invention can be made and isolated using any method known in the art, and the invention provides a few exemplary means for generating such proteins.

The peptides of the invention can also be synthesized, whole or in part, using chemical methods well known in the art (see e.g., Caruthers (1980) Nucleic Acids Res. Symp. Ser. 215–223; Horn (1980) Nucleic Acids Res. Symp. Ser. 225–232; Banga, A. K., Therapeutic Peptides and Proteins, Formulation, Processing and Delivery Systems (1995) Technomic Publishing Co., Lancaster, Pa. ("Banga")). For example, peptide synthesis can be performed using various solid-phase techniques (see e.g., Roberge (1995) Science 269:202; Merrifield (1997) Methods Enzymol. 289:3–13) and automated synthesis may be achieved, e.g., using the ABI 431A Peptide Synthesizer (Perkin Elmer) in accordance with the instructions provided by the manufacturer.

The skilled artisan will recognize that individual synthetic residues and polypeptides incorporating mimetics can be synthesized using a variety of procedures and methodologies, which are well described in the scientific and patent literature, e.g., Organic Syntheses Collective Volumes, Gilman, et al. (Eds) John Wiley & Sons, Inc., NY. Polypeptides incorporating mimetics can also be made using solid phase synthetic procedures, as described, e.g., by Di Marchi, et al., U.S. Pat. No. 5,422,426. Peptides and peptide mimetics of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi (1998) Mol. Biotechnol. 9:205–223; Hruby (1997) Curr. Opin. Chem. Biol. 1:114–119; Ostergaard (1997) Mol. Divers. 3:17–27; Ostresh (1996) Methods Enzymol. 267:220–234. Modified peptides of the invention can be further produced by chemical modification methods, see, e.g., Belousov (1997) Nucleic Acids Res. 25:3440–3444; Frenkel (1995) Free Radic. Biol. Med. 19:373–380; Blommers (1994) Biochemistry 33:7886–7896.

Peptides and polypeptides capable of generating an immune response to B-NHL cells can also be isolated from a natural sources, such as a cell line expressing the appropriate DR allele or a patient of the appropriate genotype (e.g., HLA DR10), using a variety of techniques well known in the art. Suitable HLA DR molecules can be isolated from B or T cells which have been immortalized by transformation, e.g., as by B cell transformation, utilizing techniques known in the art. See, e.g., Rothenhausler (1990) Proc. Natl. Acad. Sci. U.S.A. 87:352–354; Gorga (1987) J. Biol. Chem. 262:16087–16094; Dommair (1989) Cold Spring Harbor Symp. Quant. Biol. 54:409–416; Banga.

Fusion Proteins

Lym-1 reactive peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate Lym-1 epitope-reactive antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between the purification domain and Lym-1 reactive peptide or polypeptide can be useful to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787–1797; Dobeli (1998) Protein Expr. Purif. 12:404–14). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441–53.

Peptide Secondary Structure

Previous work has shown that Lym-1 binds the isolated Class II DR10 beta chain, but only when the intrachain disulfide bonds are intact (Rose (1996) supra). An affinity column using immobilized Lym-1 antibody isolated the Lym-1 antigen from a Raji cell lysate. Characterization of immunoaffinity-purified Lym-1 antigen on Western blots demonstrated it to be the beta chain of HLA DR10. However, the Raji cell Lym-1 antigen is only recognized by Lym-1 antibody if the beta chain (intra-chain) disulfide bonds are intact. These results demonstrate that, at least in some cells, Lym-1 antibody binds a discontinuous epitope, i.e., binds to a conformational epitope formed by the folding of the polypeptide induced by intra-molecular disulfide bonding.

Figure 1:
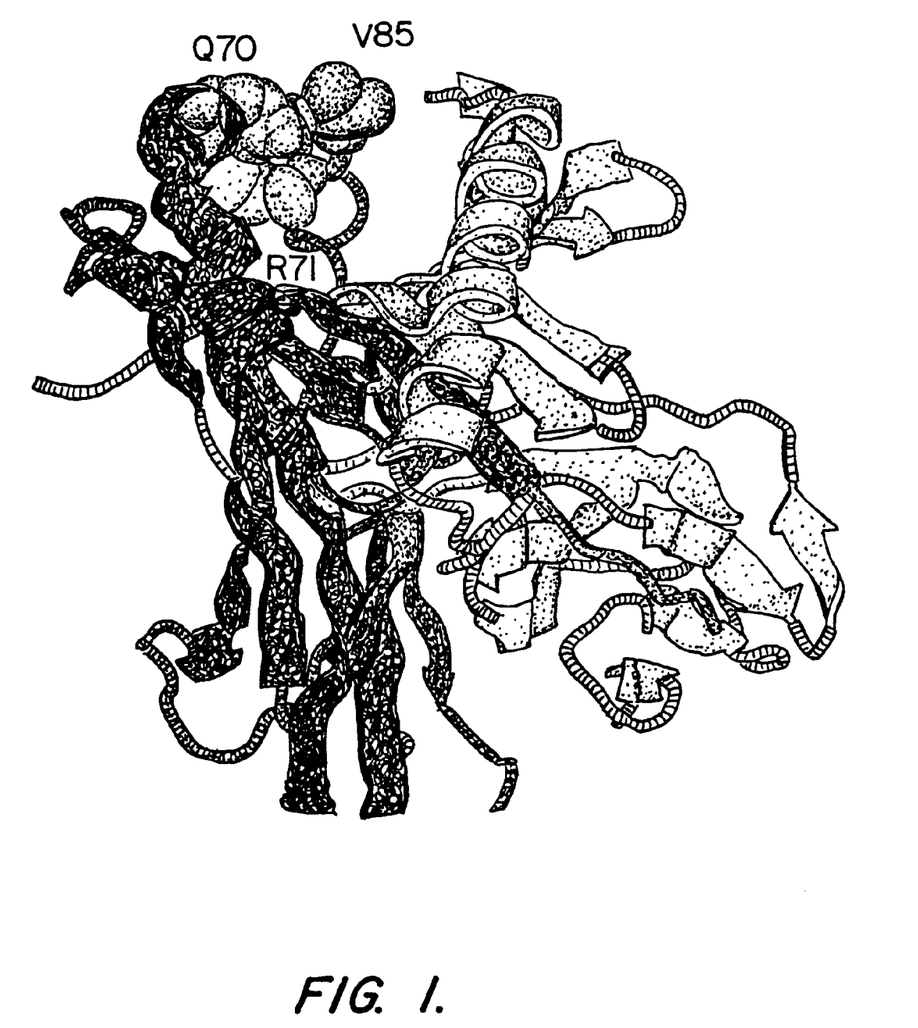
FIG. 1 shows a schematic illustration of the critical Lym-1 binding residues on the HLA Class II allele, DR1, as described in further detail, below.

As identified by the present invention, in the Raji cell DR10 Lym-1 epitope, the intra-chain disulfide bond is formed between residues 15 and 79, which brings a valine at residue 85 in relatively close proximity to an arginine at residue 71; see the analogous three dimensional structure of a DR antigen in Brown (1993) Nature 364:33–39, in FIG. 1, from which the distances between the residues of the Lym-1 epitope can be estimated.

This invention has, for the first time, determined the epitope for the Lym-1 antibody on Class II DR10 polypeptides is $R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$, where $R_1$ is Gln, Lys, or Arg; $R_2$ is Arg; $R_3$ is Arg; $R_4$ is Ala; $R_5$ is Ala; $R_6$ is Val; $R_7$ is Asp; $R_8$ is Thr; $R_9$ is Tyr; $R_{10}$ is Cys; $R_{11}$ is Arg; $R_{12}$ is His; $R_{13}$ is Asn; $R_{14}$ is Tyr; $R_{15}$ is Gly, and $R_{16}$ is Val, or, simply: (Gln Lys, or Arg)-Arg-Arg-Ala-Ala-Val-Asp-Thr-Tyr-Cys-Arg-His-Asn-Tyr-Gly-Val (SEQ ID NO: 2), which correspond to residues 70 to 85 on the DR10 polypeptide. Based on the secondary structure of DR molecules proposed by Brown (1993) supra, (see FIG. 1), in DR10, the valine at residue 85 in proximity to the arginine at residue 71 (because of the secondary structure induced by the intrachain disulfide bond) corresponds to residue $R_{16}$ and residue $R_2$, respectively, of the epitope of the invention. Accordingly, in one embodiment, the invention provides a polypeptide or peptide composition which, in addition to having the above-described amino acid sequence, has a secondary structure in the same orientation with respect to each other as in the native molecule (estimated by the teaching of, e.g., the DR structure proposed by Brown (1993) supra). One of skill can readily test whether (and to what degree, i.e., what with what affinity) a peptide with a particular secondary structure binds to Lym-1 antibody.

Peptidomimetics (i.e., completely or partially synthetic peptides) of the invention can be designed to incorporate secondary structure. For example, the design can ensure that, in the folded peptidomimetic, two particular residues are a predesignated distance from one another. Thus, a peptidomimetic of the invention can be designed to fold to have residues $R_{16}$ and residue $R_2$ the same distance apart as they would be in the native Class II DR structure, as discussed above. Beta turns, beta sheets, alpha helix structures, gamma turns, and the like can be incorporated into the peptidomimetic to effect this, or any other, design. For example, substitution of natural amino acid residues with D-amino acids; N-alpha-methyl amino acids; C-alpha-methyl amino acids; or dehydroamino acids within a peptide can induce or stabilize beta turns, gamma turns, beta sheets or alpha helix conformations. Beta turn mimetic structures have been described, e.g., by Nagai (1985) Tet. Lett. 26:647–650; Feigl (1986) J. Amer. Chem. Soc. 108:181–182; Kahn (1988) J. Amer. Chem. Soc. 110:1638–1639; Kemp (1988) Tet. Lett. 29:5057–5060; Kahn (1988) J. Molec. Recognition 1:75–79. Beta sheet mimetic structures have been described, e.g., by Smith (1992) J. Amer. Chem. Soc. 114:10672–10674; Banerjee (1996) Biopolymers 39:769–777. Secondary structures of polypeptides can be analyzed by, e.g., high-field 1H NMR or 2D NMR spectroscopy, see, e.g., Higgins (1997) J. Pept. Res. 50:421–435. See also, Hruby (1997) Biopolymers 43:219–266, Balaji, et al., U.S. Pat. No. 5,612,895.

Generation of an Anti-B-NHL Immune Response

The Lym-1 reactive peptides and polypeptides of the invention can also be used to generate an immune response against Lym-1 epitope-expressing B-NHL cells. In one embodiment, they are used to generate antibodies with equal or greater affinity than Lym-1 to epitope-expressing B-NHL cells. These antibodies can react with B-cell chronic lymphocytic leukemia/small lymphocytic lymphomas (B-CCL/SLL), lympho-plasmacytoid lymphomas (LPL), follicular lymphomas (FL), mucosa-associated lymphoid tissue lymphomas (MALTL), splenic lymphoma with villous lymphocytes (SLVL), or mantle cell lymphomas. Such antibodies can be generated in vitro, e.g., using recombinant antibody binding site expressing phage display libraries, or in vivo, e.g., using animals. Such recombinant anti-B-NHL antibodies can be further "humanized" for administration to patients with Lym-1 epitope-expressing B-NHL. Methods for making chimeric, e.g., "humanized," antibodies are well known in the art, see e.g., Wallace, et. al., U.S. Pat. No. 5,811,522; Leung, et. al., U.S. Pat. No. 5,789,554.

In one embodiment, the peptides of the invention are used as a pharmaceutical, immunogenic composition to generate an anti-Lym-1 expressing-B-NHL response in a human. The peptide can be conjugated to another molecule or can be administered with an adjuvant. Alternatively, DNA encoding a polypeptide comprising the Lym-1 epitope of the invention can be administered as a pharmaceutical. The coding sequence is part of an expression cassette or vector capable of expressing the immunogen in vivo. (see, e.g., Katsumi (1994) Hum. Gene Ther. 5:1335–9).

The immunogenic compositions of the invention can generate an anti-Lym-1 epitope specific cellular or a humoral (antibody) immune response.

The peptides of the invention can also be used to isolate, detect or quantify newly generated or existing anti-Lym-1 reactive antibodies, or to detect a cellular immune response.

Methods of producing polyclonal and monoclonal antibodies are known to those of skill in the art and described in the scientific and patent literature, see, e.g., Coligan, Current Protocols in Immunology, Wiley/Greene, NY (1991); Stites (eds.) Basic and Clinical Immunology (7th ed.) Lange Medical Publications, Los Altos, Calif. ("Stites"); Goding, Monoclonal Antibodies: Principles and Practice (2d ed.) Academic Press, New York, N.Y. (1986); Kohler (1975) Nature 256:495; Harlow (1988) Antibodies, a Laboratory Manual, Cold Spring Harbor Publications, New York.

Such techniques include selection of Lym-1 reactive antibodies from libraries of recombinant antibodies displayed on phage ("phage display libraries") or on cells. See, e.g., Huse (1989) Science 246:1275; Ward (1989) Nature 341:544; Hoogenboom (1997) Trends Biotechnol. 15:62–70; Katz (1997) Annu. Rev. Biophys. Biomol. Struct. 26:27–45. Recombinant antibodies can also be expressed by transient or stable expression vectors in mammalian cells, as in Norderhaug (1997) J. Immunol. Methods 204:77–87; Boder (1997) Nat. Biotechnol. 15:553–557.

Specific monoclonal and polyclonal antibodies and antisera will usually bind with a $K_D$ of at least about 1 $\mu$M, preferably at least about 0.1 $\mu$M or better, and most preferably, 0.01 $\mu$M or better.

Immunoassays

The invention provides a composition which, when administered in an immunogenically effective amount to a mammal, is capable of generating an antibody reactive with a Lym-1 epitope expressing B-NHL cell. The invention also provides a method for detecting an antibody reactive with a Lym-1 epitope expressing B-NHL cell using a peptide of the invention. Accordingly, the invention also provides reagents and methods using a variety of antibody based assays.

Immunological binding are well known in the art; see, e.g., U.S. Pat. Nos. 4,366,241; 4,376,110; 4,517,288; and 4,837,168; Methods in Cell Biology Vol. 37. Antibodies in Cell Biology, Asai, ed. Academic Press, Inc. New York (1993); Sambrook, Stites; Silzel (1998) Clin. Chem. 44:2036–43; Rongen (1997) J. Immunol. Methods 204:105–133.; Hashida (1995) Biotechnol. Annu. Rev. 1:403–51; Bao (1997) J. Chromatogr. B. Biomed. Sci. Appl. 699:463–80; Self (1996) Curr. Opin. Biotechnol. 7:60–5.

Formulation and Administration of Peptide Pharmaceutical Compositions

The invention also provides an immunogenic composition comprising a peptide epitope of the invention capable of eliciting an immunogenic response to that epitope. In one embodiment, the peptides and polypeptides of the invention are administered with a pharmaceutically acceptable carrier (s) (excipient) to form the pharmacological composition.

Pharmaceutically acceptable carriers and formulations for peptides and polypeptide are known to the skilled artisan and are described in detail in the scientific and patent literature, see e.g., the latest edition of Remington's Pharmaceutical Science, Maack Publishing Company, Easton, Pa. ("Remington's"); Banga; Putney (1998) Nat. Biotechnol. 16:153–157; Patton (1998) Biotechniques 16:141–143; Edwards (1997) Science 276: 1868–1871; Ho, et al., U.S. Pat. No. 5,780,431; Webb, et al., U.S. Pat. No. 5,770,700; Goulmy, et. al., U.S. Pat. No. 5,770,201.

The peptide and polypeptide immunogenic compositions used in the methods of the invention can be delivered alone or as pharmaceutical compositions by any means known in the art, e.g., systemically, regionally, or locally; by intraarterial, intrathecal (IT), intravenous (IV), parenteral, intra-pleural cavity, topical, oral, or local administration, as subcutaneous, intra-tracheal (e.g., by aerosol) or transmucosal (e.g., buccal, bladder, vaginal, uterine, rectal, nasal mucosa). Actual methods for delivering compositions will be known or apparent to those skilled in the art and are described in detail in the scientific and patent literature, see e.g., Remington's.

The pharmaceutical compositions can be administered by any immunization protocol and in a variety of unit dosage forms depending upon the method of administration, whether an initial or booster dose is being administered, and the like. Immunogenic dosages for typical peptide and polypeptide pharmaceutical compositions are well known to those of skill in the art. Such dosages are typically advisorial in nature and are adjusted depending on a variety of factors, e.g., the initial immune response (e.g., antibody titers after initial immunization), the particular therapeutic context, patient health and tolerance. The amount of peptide adequate to generate the desired immune response is defined as a "therapeutically effective dose." The immunization and dosage schedule and amounts effective for this use, i.e., the "dosing regimen," will depend upon a variety of factors, including the stage of the B-NHL, the severity of the disease or condition, the general state of the patient's health, the patient's physical status, age, pharmaceutical formulation and concentration of immunogen and/or adjuvant, and the like. The dosage regimen also takes into consideration pharmacokinetics, i.e., the peptide pharmaceutical composition's rate of absorption, bioavailability, metabolism, clearance, and the like, see, e.g., Remington.

The immunogenic composition can be repeated ("boosters") in intervals over weeks or months, depending on the patient's condition and initial immune response.

Dosages can be determined empirically, by assessing the abatement or amelioration of symptoms, or by objective criteria, such analysis of blood or histopathology specimens. Successful treatment can also be monitored by histopathology. Thus, the immunogenic compositions of the invention are administered to, e.g., arrest the progress, reduce the severity, or prevent the recurrence of the Lym-1 epitope-expressing B-NHL.

The pharmaceutical compositions containing the peptide and complexes of the invention can be administered alone or in conjunction with other therapeutic treatments. As noted above, a single or multiple administrations (immunizations) of the compositions may be administered depending on the dosage and frequency as required and tolerated by the patient.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are offered to illustrate, but not to limit the claimed invention.

Example 1

Identification of Peptide Epitopes Reactive With Anti-B-NHL Antibodies

The following example details the identification of a novel class of peptide epitopes reactive with the Lym-1 antibody.

The Lym-1 antibody was selected to initially identify an exemplary an epitope capable of generating an anti-B-NHL immune response because this monoclonal antibody can react with most classes of B-NHL cells. As noted above, Lym-1 is a murine $IgG_{2a}$ monoclonal antibody (mAb) that selectively binds an antigen which is highly expressed on the surface of most malignant human B-cells.

An HLA-DR10 allele present on a Raji cell line was the original antigen used to generate the Lym-1 murine monoclonal antibody. However, HLA-DR10 is a relatively rare subtype found in less than 2% of the American population, while greater than 80% of lymphoma patients screened for inclusion in Lym-1 radioimmunotherapy clinical trials were Lym-1 reactive as determined by flow cytometry, immunoperoxidase staining and radioimmunodiagnostic imaging. This demonstrates that Lym-1 reacts with at least one epitope that is present in some HLA-DR10 alleles, but also with many other, but not all HLA-DR alleles. Thus, the data supports the existence of several different Lym-1 reactive, and thus anti-B-NHL reactive, epitopes on many different DR beta chain alleles. The present invention, as described below, for the first time, identifies this novel class of epitopes.

The basic strategy of these studies exploited the existence of over 100 polymorphic variants of the human DR beta chains to design epitope mapping experiments (see, e.g., Erlich (1991) Hum. Immunol. 30:110–118).

Lymphoma Biopsy Studies

To structurally analyze polymorphic variants of the DR beta chains reactive with Lym-1, Class II DR encoding nucleic acid amplified from lymphoma cell lines and fresh cell isolates were analyzed. Lym-1 reactive lymphoma biopsies was used for PCR based, HLA-DR subtyping (carried out essentially as described by Bunce (1995) Tissue Antigen 46:355). The amino acid sequences of the resultant set of HLA-DR subtypes for each biopsy were used to construct a set of critical Lym-1 binding residues. A rare lymphoma biopsy that was not reactive with Lym-1 was used as a negative control, to confirm that the critical residues were not present in its HLA-DR alleles.

For the lymphoma biopsy study, ten Lym-1 reactive and one Lym-1 unreactive frozen biopsied lymphoma samples were used for PCR based HLA-DR subtyping. The biopsies had been previously screened for Lym-1 reactivity by immunoperoxidase staining. A score of greater than 20% cells stained was used as the lower limit for the Lym-1 reactive group. To isolate DNA and RNA from this tumor tissue, about 10 mg of fixed frozen tissue (stored at minus 70° C.) was removed and sectioned. The resulting frozen pieces were pulverized with a Gibco stainless steel pulverized that had been precooled in liquid nitrogen for 5 min. The Gibco Triazol protocol (see, e.g., Sewall (1998) Gibco Focus Vol 20.2) was used to isolate the RNA, DNA, and protein from the tissue samples.

The nucleic acid isolated and purified from fresh frozen lymphoma tumor tissue biopsies was amplified by polymerase chain reaction (PCR). Biotinylated primers were used to amplify exon 2 of the Class II DRB2, DRB3, DRB4, and DRB5 genes. This subtyping system is based on the hybridization of biotinylated PCR products from exon 2 with immobilized sequence specific oligonucleotides. The primers and detection system were purchased as a kit (Inna-Lipa system, Murex Diagnostics Inc., Norcross, Ga.) and used according to the manufacturer's instruction.

To analyze HL4-DR subtyping results, the amino acid sequences of all possible HLA-DR alleles indicated by the DR subtyping analysis of each biopsy were treated as a set and the HLA-DR subtypes contained in these sequences were compared to the critical binding residues that are present in Lym-1 reactive HLA-DR10 beta chain, but absent in the sequences of Lym-1 unreactive DR3 and DR52 beta chains.

Only 1 of the 11 lymphoma biopsy samples was homozygous for a single HLA-DR. Interestingly, none of the eleven biopsy tissues expressed the rare HLA-DR10 allele (the original immunogen), while seven of the ten Lym-1 reactive patients expressed DR53.

The amino acid sequence of Q70 or R70 followed by R71 (Q/R70–R71) was found in all 10 of the Lym-1 reactive samples and was absent in the one Lym-1 unreactive biopsy. The Lym-1 unreactive biopsy was homozygous for HLA-DR1(0103). In summary, all of the Lym-1 reactive biopsies expressed at least one HLA-DR allele that contained the following set of putative critical Lym-1 binding residues: Q/R70, R71, A73, T77, and G86, that are contained in DR10 but not in DR3 or DR52. However A73, T77, and G86 are all contained in the alleles expressed by the Lym-1 unreactive biopsy, leaving only Q/R70–R71 as the common Lym-1 binding residues in this biopsy sampling.

Complement Dependent Cytotoxicity Assays

To confirm the results of the lymphoma biopsy study, complement dependent cytotoxicity assays were used to test a variety of naturally occurring substitutions of the critical Lym-1 binding residues (these tests were conducted essentially as described by Brown, et. al., "HLA-DR and DQ Serotyping; in Handbook of HLA Typing Techniques, ed. Hiu, et. al, CRC Press). Cells expressing known HLA-DR subtypes were assayed for Lym-1 reactivity. The complement dependent cytotoxicity assays included 37 lymphoblastoid cell lines and peripheral blood lymphocytes (PBL) from 35 healthy donors and 50 chronic lymphocytic leukemia (CLL) patients.

For the complement dependent cytotoxicity assay of lymphoblastoid cell lines, a total of 37 lymphoblastoid cell lines were assayed. These included 11 heterozygous lines and 26 homozygous lines, all of which were known to express certain HLA-DR alleles. Cell lines were assayed at concentrations of Lym-1 mAb ranging from 0.1 mg/ml to about 0.1 ug/mL. This corresponds to a concentration range of approximately 0.67 uM to 0.65 nM of Lym-1 mAb.

Complement dependent cytotoxicity assays were also conducted on fresh lymphocyte isolates. Peripheral blood lymphocytes (PBL) from healthy donors and from chronic lymphocytic leukemia (CLL) patients were isolated. A total of 85 samples of PBLs were assayed including 50 samples from CLL patients and 35 from healthy donors. PBLs were assayed at concentrations of Lym-1 mAb ranging from 0.1 mg/ml to about 6 ug/ml, which corresponds to a concentration range of approximately 0.67 uM to 42 nM of Lym-1 mAb. Lower concentrations were not used as the PBLs from both normal donors and CLL patients are much less reactive than lymphoblastoid cell lines.

For the cytotoxicity test scoring, each dilution was assessed by eye and given a score of 1, 2, 4, 6, or 8, as is the normal convention in HLA serotyping cytotoxicity assays (see Brown, et al., Handbook of HLA Typing Techniques, supra). The value "1" was assigned to correspond to 0–10% cell death, "2" was assigned to correspond to 10–20% cell death, "4" was assigned to correspond to 20–30% cell death, 6 was assigned to correspond to 30–80% cell death, and 8 was assigned to correspond to 80–100% cell death. The mean of each range was used as the percent cell death corresponding to that score. A score of 1 is taken to indicate 5% cell death (the mean of the 0–10% range), a score of 2 is taken to indicate 15% cell death (the mean of the 10–20% range), 4 is taken to indicate 25% (the mean of the 20–30% range), 6 indicates 55% cell death (the mean of the 30–80% range), 8 indicates 90% cell death (the mean of the 80–100% range). All scores (translated to mean percentage) were plotted (on a y axis) against a multiple of the log of the mAb concentration (on the x axis). A sigmoid dose response curve resulted for each dilution series. The limits of 1 and 8 are usual scores for several extremely high or low dilutions in the series. From this sigmoid curve the Lethal Dose that killed 50% (LD50) of the cells was interpolated.

To convert LD50 to $K_d$ and delta G (change in free energy) of avidity, the equilibrium equation (A+B)<=>(A·B) can be arranged to give the dissociation constant $K_d$=[A]*[B]/[A·B]. When [B] is equal to [A·B], 50% of the antigens are bound by the mAb and [B]/[A·B] cancels out leaving $K_d$=[A]50. The concentration of mAb at LD50 can then be converted to a free energy of binding by use of the equation delta G=−RT1nK. The values can be expressed in kilojoules/mole (kJ/mol) or kilocalories/mole (kCal/mol). It is assumed that the lymphoblastoid cell lines used here have comparable amounts of cell surface antigen and cytotoxicity response. Delta G refers to avidity rather than affinity here, because each mAb has two binding sites. The cell lines were ranked from highest to lowest avidity based on LD50 data. The ranking was analyzed using StatXact.3 software (Cytel Software Corp., Cambridge, Mass.)

This analysis of the complement dependent cytotoxicity assays demonstrated that (in results similar to the biopsy DR beta chain structural analysis) the only region that is, in this sampling of cells, always present in the reactive alleles and almost always absent in the unreactive alleles is Q/R70–R71. Surprisingly, in addition to Q/R70–R71, V85 also appears to be necessary for Lym-1 binding, as demonstrated by low the avidity of HLA-DR102.

In summary, fifty chronic lymphocytic leukemia (CLL) cell samples and 35 peripheral blood lymphocytes (PBL) samples from healthy donors were subtyped for HLA-DR alleles. They were also tested for Lym-1 reactivity. Lym-1 reacted similarly with PBLs and CLLS, demonstrating much lower avidities for both healthy PBLs, and CLLS, than for the lymphoblastoid cell lines tested. Lym-1 was completely unreactive with approximately 75% of the PBL and CLL samples tested (64 out of 85). Lym-1 showed the greatest avidity for three PBL samples ($1.8 \times 10^8$) and one CLL cell line ($1.1 \times 10^8$) and very weak avidity (0.1 to $0.5 \times 10^8$) for 17 other PBL samples and CLL cell lines. 20 of the 21 reactive cells expressed HLA-DR alleles containing Q/R70–R71 and V85. However, about half of the 64 unreactive PBLs and CLLs tested also contained these residues. It appears from these results that the critical Lym-1 binding residues are necessary for Lym-1 binding but that a second parameter, perhaps a threshold antigen density, is also important.

Summary

The Lym-1 reactive patient data demonstrates that, for the cells tested, critical Lym-1 binding residues are Q/R70–R71, A73, T77, and G86. These are the residues that are included in the set of the differences between the amino acid sequences of (Lym-1 reactive) DR10 and (Lym-1 unreactive) DR3 & DR52. These residues are also the amino acid sequences of the haplotypes of all ten Lym-1 reactive lymphoma biopsies tested. However, the Lym-1 unreactive biopsy contained all of the putative critical Lym-1 binding residues except Q/R70–R71. This demonstrates that the presence of A73, T77, and G86 is not sufficient for Lym-1 binding and that the sequence Q/R70–R71 is critical for Lym-1 binding to the HLA-DR alleles tested.

To confirm these results, Lym-1 was tested with a number of homozygous and heterozygous cell lines in complement dependent cytotoxicity assays. Thirty-seven lymphoblastoid cell lines, including thirty-one HLA-DR genotypes, were screened for Lym-1 reactivity. The results confirmed that all of the strongly reactive cells expressed at least one Q/R70–R71-containing HLA-DR allele, while none of the least reactive cell lines expressed that sequence at positions 70 to 71 of the DR beta chain. Cell lines containing the DR53 allele were always reactive. DR53 beta chains (DRB4-01011 and 0103) and DR10 beta chain (DRB1-1001) contain identical sequences between positions 49 to 73.

One false positive and one false negative were found in the weakly reactive categories. The results were ranked and statistically analyzed using StatXact.3 software. This analysis tests the significance of ranked data and the probability that the ranking could have resulted by chance. The simple hypothesis, based on biopsy study results, which states that the presence of Q/R70–R71 is critical for Lym-1 binding to HLA-DR was tested. The null hypothesis, which states that the cytotoxicity assay ranking could have occurred by chance, was rejected at a confidence level>>0.999.

An anomaly was found with HLA-DRB1*0102 (DR102). DR102 contains the critical Q/R70–R71 sequence, but it is not strongly reactive with Lym-1. DR102 is identical to the highly reactive DRB1*0101 (DR101) with the exception of residues 85 and 86. In DR102 the V85–G86 of DR101 has been replaced by A85–V86. This difference is apparently enough to reduce the avidity of Lym-1 for DR102. It should be noted that two other of the weakest binding cell types also express alleles that contain the A85–V86 replacement, while none of the strongest binders contain A85–V86. However, V86 is a common substitution found in both strong and weak Lym-1 binding alleles and is therefore ruled out as a critical residue, leaving V85 as a critical Lym-1 binding residue.

The sequences of the HLA-DR alleles with highest and lowest Lym-1 avidity were compared. Three residues, Q/R70, R71 and V85, are found in all of the high avidity alleles and none of the low avidity alleles. K71 appears in the sequence of the DR4 allele; however, it could not be verified whether this Q70–K71 sequence is reactive since the highly reactive DR53 allele, which contains R70–R71, is co-expressed with HLA-DR4 in all the cell lines tested. Residues Q70–K71 also appears in the sequences of several low avidity alleles, particularly, DR3 and DR52.

Therefore, for the cells tested, critical residues for strong Lym-1 binding to the HLA-DR beta chain are Q/R70–R71 and V85. These residues appear solvent exposed and oriented on the same face of the alpha helix of HLA-DR beta chain (see FIG. 1, schematically illustrating critical Lym-1 binding residues on HLA-DRI, the three dimensional structure from the Brookhaven Protein Data Bank (available, e.g., at http://pdb.pdb.bnl.gov/) file of the HLA-DR crystal structure by Brown (1993) supra. The DR beta sequence D70–R71 is unreactive, D70 apparently negating the critical Lym-1 binding residue R71. The sequence D70–E71 is unreactive, as might be expected because of the double negative charge. Alleles DR15 and 16 display Q70–A71, a net neutral charge, and show no detectable Lym-1 binding.

To summarize, a net neutral (Q70–A71, D70–R71) or negative charge (D70–E71) at residues 70–71 drastically reduces Lym-1 binding. A net positive charge (Q70–R71, R70–R71) at these positions appears to be critical for Lym-1 binding. Thus, the Lym-1 epitope can present a negative or neutral residue to the Class II molecule's antigen binding pocket.

The avidity constants measured here of Lym-1 with various cell lines are in general agreement with Epstein's avidity calculation for Lym-1 binding to Raji (Epstein (1987) supra). They found that Lym-1 binds preferentially to lymphoblastoid cells with an avidity of $4.0 \times 10^8$, which is 5-fold greater than the avidity of $0.8 \times 10^8$ they found for Lym-1 binding to healthy tonsil B-cells. Results from the instant studies show the top 16 Lym-1 binding cell lines ranged in avidity from a maximum of approximately $7.4 \times 10^8$ (DR804/9/53 and DR10/1202/52), to minimum of about $0.5 \times 10^8$. Of this group, 14 cell lines express at least one allele that contains the residues Q/R70–R71 and V85. In contrast only 1 of the 21 genotypes with avidity of less than about $0.5 \times 10^8$ has an allele that contains the critical residues (a false negative).

Lymphoblastoid cell lines are known to express much higher surface antigen density than normal peripheral blood cells. These results are also in general agreement with results from Epstein's studies (Epstein (1987) supra), which showed Lym-1 binding selectively to lymphomas as compared to normal healthy tonsil B-cells. The results from the instant cytotoxicity tests of Lym-1 with PBLs from healthy donors and CLL patients showed that these cells were much less reactive, regardless of whether they contained the Q/R70–R71 & V85 epitope. This may infer that although the critical Lym-1 binding residues are necessary, cell surface antigen density may also be useful in assessing for clinically useful avidity.

What is claimed is:

1. An isolated peptide consisting of a subsequence of a Class II major histocompatibility molecule, wherein the peptide has the following properties,
   (a) having a structure comprising $R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$,
   wherein $R_1$ is Gln, Lys, or Arg; $R_2$ is Arg; $R_3$ and $R_4$ are members independently selected from the group consisting of all amino acids; $R_5$ is Ala, Glu, Asp, Val, Leu or Ile; $R_6$ and $R_7$ are members independently selected from the group consisting of all amino acids; $R_8$ is Thr; $R_9$, $R_{10}$, $R_{11}$, $R_{12}$, $R_{13}$, $R_{14}$, and $R_{15}$ are members independently selected from the group consisting of all amino acids; and, $R_{16}$ is Val;
   (b) capable of generating an immune response to a non-Hodgkin's B cell lymphoma cell.

2. The isolated peptide of claim 1, wherein $R_1$ is Gln, Lys, or Arg; $R_2$ is Arg; $R_3$ is Arg; $R_4$ is selected from the group consisting of all amino acids; $R_5$ is Ala; $R_6$ and $R_7$ are members independently selected from the group consisting of all amino acids; $R_8$ is Thr; $R_9$ is selected from the group consisting of all amino acids; $R_{10}$ is Cys; $R_{11}$, $R_{12}$, $R_{13}$, $R_{14}$, and $R_{15}$ are members independently selected from the group consisting of all amino acids; and, $R_{16}$ is Val (SEQ ID NO: 1).

3. The isolated peptide of claim 2, wherein $R_1$ is Gln, Lys, or Arg; $R_2$ is Arg; $R_3$ is Arg; $R_4$ is Ala; $R_5$ is Ala; $R_6$ is Val; $R_7$ is Asp; $R_8$ is Thr; $R_9$ is Tyr; $R_{10}$ is Cys; $R_{11}$ is Arg; $R_{12}$ is His; $R_{13}$ is Asn; $R_{14}$ is Tyr; $R_{15}$ is Gly, and $R_{16}$ is Val (SEQ ID NO: 2).

4. The isolated peptide of claim 1, further comprising a pharmaceutically acceptable excipient.

5. A composition comprising an adjuvant and the isolated peptide of claim 1.

6. The isolated peptide of claim 1, wherein the non-Hodgkin's lymphoma cell is selected from the group consisting of a B-cell chronic lymphocytic leukemia/small lymphocytic lymphoma (B-CCL/SLL) cell, a lymphoplasmacytoid lymphoma (LPL) cell, a follicular lymphoma (FL) cell, a mucosa-associated lymphoid tissue lymphoma (MALTL) cell, a splenic lymphoma with villous lymphocytes (SLVL) cell and a mantle cell lymphoma cell.

7. A method for generating an antibody reactive with a non-Hodgkin's B cell lymphoma cell, comprising administering an immunogenically effective amount of a isolated peptide of claim 1 to a mammal.

8. The method of claim 7, wherein $R_1$ is Gln, Lys, or Arg; $R_2$ is Arg; $R_3$ is Arg; $R_4$ is Ala; $R_5$ is Ala; $R_6$ is Val; $R_7$ is Asp; $R_8$ is Thr; $R_9$ is Tyr; $R_{10}$ is Cys; $R_{11}$ is Arg; $R_{12}$ is His; $R_{13}$ is Asn; $R_{14}$ is Tyr; $R_{15}$ is Gly, and $R_{16}$ is Val (SEQ ID NO: 2).

9. The method of claim 7, wherein the non-Hodgkin's lymphoma cell is selected from the group consisting of a B-cell chronic lymphocytic leukemia/small lymphocytic lymphoma (B-CCL/SLL) cell, a lymphoplasmacytoid lymphoma (LPL) cell, a follicular lymphoma (FL) cell, a mucosa-associated lymphoid tissue lymphoma (MALTL) cell, a splenic lymphoma with villous lymphocytes (SLVL) cell and a mantle cell lymphoma cell.

10. A method of inducing an immunogenic response directed to a polypeptide epitope, comprising administering an immunogenically effective amount of a composition comprising a polypeptide epitope to a mammal,
   wherein the epitope comprises an amino acid sequence having a structure comprising $R_1$-$R_2$-$R_3$-$R_4$-$R_5$-$R_6$-$R_7$-$R_8$-$R_9$-$R_{10}$-$R_{11}$-$R_{12}$-$R_{13}$-$R_{14}$-$R_{15}$-$R_{16}$,
   wherein $R_1$ is Gln, Lys, or Arg; $R_2$ is Arg; $R_3$ and $R_4$ are members independently selected from the group consisting of all amino acids; $R_5$ is Ala, Glu, Asp, Val, Leu or Ile; $R_6$ and $R_7$ are members independently selected from the group consisting of all amino acids; $R_8$ is Thr; $R_9$, $R_{10}$, $R_{11}$, $R_{12}$, $R_{13}$, $R_{14}$, and $R_{15}$ are members independently selected from the group consisting of all amino acids; and, $R_{16}$ is Val.

11. The method of claim 10, wherein $R_1$ is Gln, Lys, or Arg; $R_2$ is Arg; $R_3$ is Arg; $R_4$ is Ala; $R_5$ is Ala; $R_6$ is Val; $R_7$ is Asp; $R_8$ is Thr; $R_9$ is Tyr; $R_{10}$ is Cys; $R_{11}$ is Arg; $R_{12}$ is His; $R_{13}$ is Asn; $R_{14}$ is Tyr; $R_{15}$ is Gly, and $R_{16}$ is Val (SEQ ID NO: 2).

12. The immunogenic method of claim 10, wherein the immunogenic response generates antibodies specific for the polypeptide epitope.

13. The method of claim 10, wherein the mammal is a human, a mouse or a rabbit.

* * * * *

SEQUENCE LISTING

<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence:subsequence
      of Class II major histocompatability molecule that generates an
      immune response to non-Hodgkin's B cell lymphoma cell
<220> FEATURE:
<221> NAME/KEY: MOD_RES
<222> LOCATION: (1)
<223> OTHER INFORMATION: Xaa = Gln, Lys or Arg
<220> FEATURE:
<221> NAME/KEY: MOD_RES -continued

```
<222> LOCATION: (4)..(16)
<223> OTHER INFORMATION: Xaa = any amino acid

<400> SEQUENCE: 1

Xaa Arg Arg Xaa Ala Xaa Xaa Thr Xaa Cys Xaa Xaa Xaa Xaa Xaa Val
 1               5                  10                  15

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence:subsequence
      of Class II major histocompatability molecule that generates an
      immune response to non-Hodgkin's B cell lymphoma cell
<220> FEATURE:
<221> NAME/KEY: MOD_RES
<222> LOCATION: (1)
<223> OTHER INFORMATION: Xaa = Gln, Lys or Arg

<400> SEQUENCE: 2

Xaa Arg Arg Ala Ala Val Asp Thr Tyr Cys Arg His Asn Tyr Gly Val
 1               5                  10                  15
```